(12) United States Patent
Obara

(10) Patent No.: US 11,685,914 B2
(45) Date of Patent: Jun. 27, 2023

(54) STABILISED DRY PROTEIN DEAMIDASE COMPOSITION

(71) Applicant: AMANO ENZYME INC., Nagoya (JP)

(72) Inventor: Takakiyo Obara, Kakamigahara (JP)

(73) Assignee: AMANO ENZYME INC., Nagoya (JP)

( * ) Notice: Subject to any disclaimer, the term of this patent is extended or adjusted under 35 U.S.C. 154(b) by 266 days.

(21) Appl. No.: 16/645,393

(22) PCT Filed: Sep. 6, 2018

(86) PCT No.: PCT/JP2018/033017
§ 371 (c)(1),
(2) Date: Mar. 6, 2020

(87) PCT Pub. No.: WO2019/049927
PCT Pub. Date: Mar. 14, 2019

(65) Prior Publication Data
US 2020/0283752 A1    Sep. 10, 2020

(30) Foreign Application Priority Data

Sep. 7, 2017 (JP) .................................. 2017-171774

(51) Int. Cl.
*C12N 9/80* (2006.01)
*C12N 9/96* (2006.01)

(52) U.S. Cl.
CPC .................. *C12N 9/96* (2013.01); *C12N 9/80* (2013.01); *C12Y 305/01044* (2013.01)

(58) Field of Classification Search
CPC ............... C12N 9/78; C12N 9/96; C12N 9/90
See application file for complete search history.

(56) References Cited

U.S. PATENT DOCUMENTS

| | | | |
|---|---|---|---|
| 3,796,633 A | 3/1974 | Kikuchi | |
| 5,275,753 A | 1/1994 | De Buzzaccarini et al. | |
| 5,827,709 A | 10/1998 | Barendse et al. | |
| 5,935,834 A | 8/1999 | Odawara et al. | |
| 5,972,669 A | 10/1999 | Barendse et al. | |
| 6,251,651 B1 | 6/2001 | Yamaguchi et al. | |
| 6,756,221 B1 | 6/2004 | Yamaguchi et al. | |
| 2004/0072318 A1 | 4/2004 | Yamaguchi et al. | |
| 2004/0166558 A1 | 8/2004 | Yamaguchi et al. | |
| 2004/0175799 A1 | 9/2004 | Yamaguchi et al. | |
| 2009/0061500 A1 | 3/2009 | Yamaguchi et al. | |
| 2009/0075337 A1 | 3/2009 | Yamaguchi et al. | |
| 2009/0081763 A1 | 3/2009 | Yamaguchi et al. | |
| 2009/0317515 A1* | 12/2009 | Lohscheidt .......... | A23K 20/189 435/187 |
| 2011/0165605 A1 | 7/2011 | Hashizume et al. | |
| 2014/0256610 A1* | 9/2014 | Hede .................. | C11D 3/38672 510/392 |
| 2015/0203796 A1* | 7/2015 | Miracle .................. | C11D 3/386 510/276 |

FOREIGN PATENT DOCUMENTS

| | | |
|---|---|---|
| CN | 1044121 A | 7/1990 |
| EP | 2 455 109 A2 | 5/2012 |
| JP | H08131171 A | 5/1996 |
| JP | H09154576 A | 6/1997 |
| JP | 2000-050887 A | 2/2000 |
| JP | 2001-218590 A | 8/2001 |
| RU | 2010-148524 A | 6/2012 |
| RU | 2559522 C2 | 6/2012 |
| WO | WO 2010-029685 A1 | 3/2010 |

OTHER PUBLICATIONS

Partial Supplementary European Search Report dated May 11, 2021 in European Patent Application No. 18853419.2.
Extended European Search Report dated Aug. 4, 2021 in European Patent Application No. 18853419.2.
Hillbrothers, Liquid Ammonium Sulfate 40% Solution, Retrieved from the Internet: URL:http://hillbrothers.com/wp-content/uploads/2016/11/LiquidAmmonium40Solution.pdf; Jul. 20, 2021.
International Preliminary Report on Patentability dated Mar. 10, 2020 in International Application No. PCT/JP2018/033017.
International Search Report and Written Opinion dated Nov. 27, 2019 in International Application No. PCT/JP2018/033017.
Shaha et al., Protein Deamidases From Germinating Seeds, Physiological Plantarum, vol. 96, pp. 622-666, 1996.
Kikuchi et al., Peptidoglutaminase, Enzymes for Selective Deamidation of-Amide of Peptide-Bound Glutamine, Biochemistry, vol. 10, pp. 1222-1229, 1971.
Kikuchi et al., Some Enzymatic Properties and Substrate Specificities of Peptidoglutaminase-I and II ,Agricultural and Biological Chemistry, vol. 37, No. 8, pp. 1813-1821,1973.
Office Action dated Feb. 11, 2023 in Chinese Patent Application No. 201880057099.5.
Wang, H. et al., Studies on stability of recombinant L-asparaginase preparations, *Pharmaceutical Biotechnology*, vol. 4, No. 2, pp. 93-97, 1997.
Koma et al., Do you know the ingredients of the culture medium?, Journal of the Society for Biotechnology, Japan, 2011, 89 Volumes, No. 4, 195-199 Pages.
Office Action dated Apr. 4, 2023 in Japanese Patent Application No. 2019-540993.

\* cited by examiner

*Primary Examiner* — Yong D Pak
(74) *Attorney, Agent, or Firm* — Knobbe, Martens, Olson & Bear LLP

(57) ABSTRACT

A technique of using a compositional innovation of a dry enzyme composition to improve the stability of a protein deamidase composition enables improvement of the stability of a dry protein deamidase composition by making both a protein deamidase and magnesium chloride coexist in a dry enzyme composition. The technique involves making adjustments so that the pH is at least 2 and less than 5 when the composition is dissolved in water at a concentration of 1 w/v %.

4 Claims, No Drawings
Specification includes a Sequence Listing.

SEQUENCE LISTING

<160> NUMBER OF SEQ ID NOS: 2

<210> SEQ ID NO 1
<211> LENGTH: 320
<212> TYPE: PRT
<213> ORGANISM: Chryseobacterium scophthalmum

<400> SEQUENCE: 1

Met Lys Asn Leu Phe Leu Ser Met Met Ala Phe Val Thr Val Leu Thr
1               5                   10                  15

Phe Asn Ser Cys Ala Asp Ser Asn Gly Asn Gln Glu Ile Asn Gly Lys
            20                  25                  30

Glu Lys Leu Ser Val Asn Asp Ser Lys Leu Lys Asp Phe Gly Lys Thr
        35                  40                  45

Val Pro Val Gly Ile Asp Glu Glu Asn Gly Met Ile Lys Val Ser Phe
    50                  55                  60

Met Leu Thr Ala Gln Phe Tyr Glu Ile Lys Pro Thr Lys Glu Asn Glu

```
                65                  70                  75                  80
        Gln Tyr Ile Gly Met Leu Arg Gln Ala Val Lys Asn Glu Ser Pro Val
                            85                  90                  95

His Ile Phe Leu Lys Pro Asn Ser Asn Glu Ile Gly Lys Val Glu Ser
                           100                 105                 110

Ala Ser Pro Glu Asp Val Arg Tyr Phe Lys Thr Ile Leu Thr Lys Glu
                           115                 120                 125

Val Lys Gly Gln Thr Asn Lys Leu Ala Ser Val Ile Pro Asp Val Ala
                           130                 135                 140

Thr Leu Asn Ser Leu Phe Asn Gln Ile Lys Asn Gln Ser Cys Gly Thr
        145                 150                 155                 160

Ser Thr Ala Ser Ser Pro Cys Ile Thr Phe Arg Tyr Pro Val Asp Gly
                           165                 170                 175

Cys Tyr Ala Arg Ala His Lys Met Arg Gln Ile Leu Met Asn Asn Gly
                           180                 185                 190

Tyr Asp Cys Glu Lys Gln Phe Val Tyr Gly Asn Leu Lys Ala Ser Thr
                           195                 200                 205

Gly Thr Cys Cys Val Ala Trp Ser Tyr His Val Ala Ile Leu Val Ser
                           210                 215                 220

Tyr Lys Asn Ala Ser Gly Val Thr Glu Lys Arg Ile Ile Asp Pro Ser
        225                 230                 235                 240

Leu Phe Ser Ser Gly Pro Val Thr Asp Thr Ala Trp Arg Asn Ala Cys
                           245                 250                 255

Val Asn Thr Ser Cys Gly Ser Ala Ser Val Ser Ser Tyr Ala Asn Thr
                           260                 265                 270

Ala Gly Asn Val Tyr Tyr Arg Ser Pro Ser Asn Ser Tyr Leu Tyr Asp
                           275                 280                 285

Asn Asn Leu Ile Asn Thr Asn Cys Val Leu Thr Lys Phe Ser Leu Leu
                           290                 295                 300

Ser Gly Cys Ser Pro Ser Pro Ala Pro Asp Val Ser Ser Cys Gly Phe
        305                 310                 315                 320

<210> SEQ ID NO 2
<211> LENGTH: 185
<212> TYPE: PRT
<213> ORGANISM: Chryseobacterium scophthalmum

<400> SEQUENCE: 2

Leu Ala Ser Val Ile Pro Asp Val Ala Thr Leu Asn Ser Leu Phe Asn
        1                   5                   10                  15

Gln Ile Lys Asn Gln Ser Cys Gly Thr Ser Thr Ala Ser Ser Pro Cys
                            20                  25                  30

Ile Thr Phe Arg Tyr Pro Val Asp Gly Cys Tyr Ala Arg Ala His Lys
                            35                  40                  45

Met Arg Gln Ile Leu Met Asn Asn Gly Tyr Asp Cys Glu Lys Gln Phe
                            50                  55                  60

Val Tyr Gly Asn Leu Lys Ala Ser Thr Gly Thr Cys Cys Val Ala Trp
        65                  70                  75                  80

Ser Tyr His Val Ala Ile Leu Val Ser Tyr Lys Asn Ala Ser Gly Val
                            85                  90                  95

Thr Glu Lys Arg Ile Ile Asp Pro Ser Leu Phe Ser Ser Gly Pro Val
                           100                 105                 110

Thr Asp Thr Ala Trp Arg Asn Ala Cys Val Asn Thr Ser Cys Gly Ser
                           115                 120                 125
```

-continued

```
Ala Ser Val Ser Ser Tyr Ala Asn Thr Ala Gly Asn Val Tyr Tyr Arg
    130             135             140
Ser Pro Ser Asn Ser Tyr Leu Tyr Asp Asn Asn Leu Ile Asn Thr Asn
145             150             155             160
Cys Val Leu Thr Lys Phe Ser Leu Leu Ser Gly Cys Ser Pro Ser Pro
            165             170             175
Ala Pro Asp Val Ser Ser Cys Gly Phe
        180             185
```

STABILISED DRY PROTEIN DEAMIDASE COMPOSITION

PRIORITY AND CROSS REFERENCE TO RELATED APPLICATIONS

This application is the U.S. National Stage Application under 35 U.S.C. § 371 of International Application No. PCT/JP2018/033017, filed Sep. 6, 2018, designating the U.S. and published as WO 2019/049927 A1 on Mar. 14, 2019, which claims the benefit of Japanese Patent Application No. JP 2017-171774, filed Sep. 7, 2017. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled LEX023004APCSEQLIST.txt, created and last modified on Mar. 5, 2020, which is 4,759 bytes in size. The information in the Electronic Sequence Listing is incorporated herein by reference in its entirety.

TECHNICAL FIELD

The present invention relates to a stabilized dry protein deamidase composition.

BACKGROUND ART

The protein deamidase assigned the EC number, EC 3.5.1.44, is an enzyme that hydrolyzes an amide group of glutamine and asparagine in a protein, thereby converting glutamine and asparagine to glutamic acid and aspartic acid, respectively, while liberating ammonia. The protein deamidase can be used in various applications such as improvement in protein functionalities (solubility, emulsification characteristics, foam characteristics, gelation characteristics, etc.), improvement in extension of dough of wheat gluten, reduction in wheat allergen induction, improvement in efficiency of protein extraction from an agricultural product, and improvement in calcium solubility in a protein solution, and thus the protein deamidase makes an enzyme with high industrial applicability.

The protein deamidases widely exist in the natural world. As the best known example, a protein glutaminase derived from a microorganism described in Patent documents 1 and 2 can be mentioned. Non-patent document 1 discloses the existence of an enzyme that deamidates a glutamine residue in a protein, originated from wheat in germination, a green bean, and a pumpkin seed. Further, Non-patent document 2 discloses the existence of a peptide glutaminase as an enzyme that deamidates a glutamine residue in a peptide, found in a bacterial cell of the bacterium (Bacillus circulans). Further, Non-patent document 2 describes that the pH stability of the protein deamidase solution is from pH 5 to 9.

Note that a transglutaminase can be mentioned as an enzyme that acts on an amide group and has been long known before the protein deamidase. The transglutaminase is an acyltransferase that is assigned the EC number, EC 2.3.2.13. The protein deamidase is known as an enzyme that is completely different from the transglutaminase in terms of structure, characteristics, and the like.

Storage stability is important when an enzyme is used as an industrial enzyme preparation. Examples of a means of maintaining sufficient storage stability include modification of characteristics of an enzyme itself by mutation and addition of a stabilizing agent.

For example, Patent document 3 describes designing of the mutant protein deamidase by introducing a specific mutation to the protein deamidase for improving stability.

PRIOR ART DOCUMENTS

Patent Documents

Patent Document 1: Japanese Patent Laid-open Publication No. 2000-50887
Patent Document 2: Japanese Patent Laid-open Publication No. 2001-218590
Patent Document 3: WO 2010/029685

Non-Patent Document

Non-Patent Document 1: Vaintraub, I. A., Kotova, L. V. & Shaha, R. (1996) Protein deamidases from germinating seeds. Physiol. Plantarum. 96, 662-666.
Non-Patent Document 2: Kikuchi, M., Hayashida, H., Nakano, E. & Sakaguchi K. (1971) Peptidoglutaminase. Enzymes for selective deamidation of γ-amido of peptide-bound glutamine. Biochemistry 10, 1222-1229.

SUMMARY

It is known that stability of the protein deamidase is improved by introducing a mutation to the enzyme itself as described in Patent document 3. However, there is no known method of improving stability of the protein deamidase by modifying a compositional condition of an enzyme composition.

Thus, an object of the present invention is to provide a technique for improving stability of a protein deamidase composition by modifying a compositional condition of an enzyme composition.

The present inventor has conducted studies on a stabilizing agent for improving stability of a protein deamidase in an enzyme composition and found that stability of the protein deamidase itself is effectively improved by preparing the protein deamidase as a dry composition which is formulated with magnesium chloride or preparing the protein deamidase as a dry composition in which the pH upon dissolution is adjusted to lower than 5. The present invention has been completed on the basis of these findings.

The present invention includes the following invention.
Section 1. A stabilized dry protein deamidase composition including a protein deamidase and magnesium chloride.
Section 2. The stabilized dry protein deamidase composition according to section 1, in which a content of the magnesium chloride is from 1.0 to 10.0% by weight.
Section 3. The stabilized dry protein deamidase composition according to section, in which a content of the magnesium chloride is from 1.0 to 6.0% by weight.
Section 4. The stabilized dry protein deamidase composition according to section 1, in which a content of the magnesium chloride is from 0.01 to 2.0 mg/u.
Section 5. A stability-improving method for improving stability of a protein deamidase in a dry enzyme composition including the protein deamidase, in which the protein deamidase coexists with the magnesium chloride in the dry enzyme composition.

Section 6. A stabilized dry protein deamidase composition having a pH of 2 or higher and lower than 5 upon dissolution in water at 1 w/v %.

Section 7. A stability-improving method for improving stability of a protein deamidase in a dry enzyme composition including the protein deamidase,
in which a pH of the dry enzyme composition upon dissolution in water at 1 w/v % is adjusted to 2 or higher and lower than 5.

Section 8. A method for producing a stabilized dry protein deamidase composition including the steps of preparing an enzyme liquid that has a pH of 2 or higher and lower than 5 and includes the protein deamidase; and drying the enzyme liquid.

According to the present invention, there is provided the technique for improving stability of the protein deamidase composition by modifying the compositional condition of the dry enzyme composition.

DETAILED DESCRIPTION

[1. Dry Protein Deamidase Composition]

The present invention provides a stabilized dry protein deamidase composition including a protein deamidase and magnesium chloride and a stabilized dry protein deamidase composition having a pH of 2 or higher and lower than 5 upon dissolution in water at a predetermined concentration. Note that the stabilized dry protein deamidase composition having a pH of 2 or higher and lower than 5 upon dissolution in water at a predetermined concentration may or may not include magnesium chloride.

[1-1. Protein Deamidase]

The protein deamidase of the present invention, which is also called protein glutaminase, is an enzyme that acts on an amide group on the side chain of a protein and hydrolyzes the amide group into a side chain carboxyl group and ammonia. The optimum temperature is, for example, about 60° C. and the optimum pH is, for example, about pH 6. Examples of an amino acid residue having a side chain amide group on which the protein deamidase acts include but are not limited to an asparagine residue and a glutamine residue. Further, as a protein serving as a substrate of the protein deamidase, a protein having a molecular weight of 5000 or more, preferably from 10,000 to 2,000,000, can be mentioned. However, a polypeptide (including a dipeptide) having a molecular weight of less than 5000 is also included. Further, a protein serving as a substrate of the protein deamidase may be in a form of a simple protein constituted only of amino acid residues or a conjugated protein conjugated with a saccharide, a lipid, or the like.

Note that the protein deamidase of the present invention acts on an amide group on the side chain of a protein without exhibiting transglutaminase activity. As seen from a transglutaminase, the transglutaminase activity catalyzes formation of an isopeptide bond between a glutamine residue and a lysine residue in proteins. Further, the protein deamidase of the present invention has no protease activity. As seen from various proteases, the protease activity hydrolyzes a peptide bond in a protein.

An organism from which the protein deamidase of the present invention is derived is not particularly limited as long as the organism can produce an enzyme that acts on an amide group on the side chain of a protein and has deamidation activity without causing cleavage of a peptide bond or crosslinking of proteins. Examples of the organism from which the protein deamidase is derived include a bacterium classified as *Cytophagales*, *Actinomycetes*, or *Flavobacteriaceae*, more specifically, a microorganism classified as *Chryseobacterium* genus, *Flavobacteium* genus, *Empedobacter* genus, *Sphingobacterium* genus, *Aureobacterium* genus, or *Myroides* genus, preferably a microorganism classified as *Chryseobacterium* genus, more preferably *Chryseobacterium* sp. No. 9670 (FERM BP-7351) classified as *Chryseobacterium* genus.

An amino acid sequence of the protein deamidase of the present invention is derived is not particularly limited as long as the protein deamidase acts on an amide group on the side chain of a protein and has deamidation activity without causing cleavage of a peptide bond or crosslinking of proteins. From the standpoint of more preferably obtaining a stability-improving effect, a protein having an amino acid sequence represented by SEQ ID No: 1 (1-135: prepro sequence, 136-320: mature form sequence), an amino acid sequence represented by SEQ ID No: 2 (the mature form sequence of the amino acid sequence represented by SEQ ID No: 1), and a protein having an amino acid sequence represented by SEQ ID No: 1 or 2 in which one or a plurality of amino acids have been deleted, substituted, inserted or added, and acting on an amide group on the side chain of a protein and having deamidation activity without causing cleavage of a peptide bond or crosslinking of proteins, can be preferably mentioned, and a protein having an amino acid sequence represented by SEQ ID No: 1 or 2 can be more preferably mentioned. Further, as long as the aforementioned activity is exhibited, the amino acid sequence of the protein deamidase may be an amino acid sequence having identity of, for example, 70% or more, preferably 80% or more, more preferably 90% or more, further more preferably 95% or more, with the amino acid sequence represented by SEQ ID No: 1 or 2. Note that the term "identity" used herein refers to a proportion (%) of identical amino acid residues with respect to all overlapping amino acid residues in the optimal alignment in which two amino acid sequences are aligned using a mathematical algorithm known in the "TECHNICAL FIELD" (preferably, the algorithm can take into consideration an introduction of a gap into one or both of the sequences for optimizing the alignment).

The molecular weight (the molecular weight by SDS polyacrylamide gel electrophoresis) of the protein deamidase is, for example, from 18,000 to 22,000, preferably about 20,000. The optimal pH of the protein deamidase is, for example, from 5 to 7, preferably from 5.5 to 6.5, more preferably about 6. The optimal pH is obtained by measuring enzyme activity as follows: 100 µl of substrate solutions (containing 10 mmol/l Z-Gln-Gly) [40 mmol/l Britton-Robinson buffer solution (pH 3 to 12)] having different pH values are preheated at 37° C. for 5 min, and then 10 µl of enzyme liquids each containing 0.32 µg of the protein deamidase are added to the substrate solutions to perform reactions at 37° C. for 60 min. The optimal temperature of the protein deamidase is, for example, from 50 to 70° C., preferably from 55 to 65° C., more preferably about 60° C. The optimal temperature is obtained by measuring enzyme activity as follows: 10 µl of enzyme liquids each containing 1.21 µg of the protein deamidase are added to 100 µl of substrate solutions (containing 10 mmol/l Z-Gin-Gly) [176 mmol/l phosphate buffer solution (pH 6.5)] to perform reactions at different temperatures for 60 min. The protein deamidase has a pH stability of, for example, from 5 to 9. The pH stability is obtained by measuring the remaining enzyme activity after 22 µl of enzyme liquids [40 mmol/l Britton-Robinson buffer solution (pH 3 to 12)] each containing 0.75 μg of the protein deamidase are treated at 30° C. for 18 hours. The protein deamidase has a temperature stability of 50° C. or less. The temperature stability is obtained by measuring the remaining enzyme activity after 43 μl of enzyme liquids [50 mmol/l phosphate buffer solution (pH 7.0)] each containing 1.76 μg of the protein deamidase are allowed to stand at different temperatures for 10 min.

The content of the protein deamidase in the dry protein deamidase composition (100% by weight) is not particularly limited. However, the content is, for example, 0.1% by weight or more, preferably 0.2% by weight or more, more preferably 0.3% by weight or more, further more preferably 0.5% by weight or more, and, for example, 20% by weight or less, preferably 10% by weight or less, more preferably 5.0% by weight or less, further more preferably 2.5% by weight or less.

[1-2. Magnesium Chloride]

The dry protein deamidase composition of the present invention can include magnesium chloride. Magnesium chloride is used as a stabilizing agent for the protein deamidase. The dry protein deamidase composition of the present invention can obtain excellent stability by using magnesium chloride as a stabilizing agent.

The content of magnesium chloride is not particularly limited. However, from the standpoint of preferably obtaining a stability-improving effect, a ratio of magnesium chloride with respect to the total weight of the dry protein deamidase composition (100% by weight) is, for example, from 1.0 to 10.0% by weight. From the standpoint of more preferably obtaining a stability-improving effect, the lower limit of a range of the above ratio with respect to the total weight of the dry protein deamidase composition is preferably 1.5% by weight or more, more preferably 2.0% by weight or more, further more preferably 2.5% by weight or more, still further more preferably 3.0% by weight or more, still further more preferably 3.5% by weight or more, particularly preferably 4.0% by weight or more, while the upper limit of the range of the ratio is preferably 9.0% by weight or less, more preferably 7.0% by weight or less, further more preferably 6.5% by weight or less. A specific range of the magnesium chloride content is, not limitatively, from 1.0 to 9.0% by weight, from 1.0 to 7.0% by weight, from 1.0 to 6.5% by weight, from 1.5 to 10.0% by weight, from 1.5 to 9.0% by weight, from 1.5 to 7.0% by weight, from 1.5 to 6.5% by weight, from 2.0 to 10.0% by weight, from 2.0 to 9.0% by weight, from 2.0 to 7.0% by weight, from 2.0 to 6.5% by weight, from 3.0 to 10.0% by weight, from 3.0 to 9.0 is by weight, from 3.0 to 7.0% by weight, from 3.0 to 6.5% by weight, from 3.5 to 10.0% by weight, from 3.5 to 9.0% by weight, from 3.5 to 7.0% by weight, from 3.5 to 6.5% by weight, from 4.0 to 10.0% by weight, from 4.0 to 9.0% by weight, from 4.0 to 7.0% by weight, or from 4.0 to 6.5% by weight.

Further, from the standpoint of preferably obtaining powder characteristics (e.g., inhibitory properties of caking and/or deliquescence) of the dry protein deamidase composition in addition to the stability-improving effect, the ratio with respect to the total weight of the dry protein deamidase composition is, for example, from 1.0 to 6.0% by weight. From the standpoint of more preferably obtaining powder characteristics (e.g., inhibitory properties of caking and/or deliquescence) of the dry protein deamidase composition, the upper limit of a range of the above ratio with respect to the total weight of the dry protein deamidase composition is preferably 5.5% by weight or less, more preferably 5.0% by weight or less, further more preferably 4.5% by weight or less, still further more preferably 4.0% by weight or less. A specific range of the magnesium chloride content, when taking into consideration the powder characteristics of the dry protein deamidase composition in addition to the stability-improving effect, is, not limitatively, from 1.0 to 5.5% by weight, 1.0 to 5.0% by weight, 1.0 to 4.5% by weight, or 1.0 to 4.0% by weight.

Further, the content of magnesium chloride is, for example, from 0.01 to 2.0 mg/u as an amount per unit activity of the protein deamidase from the standpoint of preferably obtaining the stability-improving effect. From the standpoint of more preferably obtaining the stability-improving effect, the more preferable lower limit of a range of the above amount per unit activity of the protein deamidase is, not limitatively, 0.02 mg/u or more, preferably 0.03 mg/u or more, more preferably 0.04 mg/u or more, further more preferably 0.05 mg/u or more, still further more preferably 0.06 mg/u or more, still further more preferably 0.07 mg/u or more, particularly preferably 0.08 mg/u or more, while the more preferable upper limit of the range of the amount per unit activity of the protein deamidase is, not limitatively, 1.0 mg/u or less, preferably 0.50 mg/u or less, more preferably 0.20 mg/u or less, further more preferably 0.18 mg/u or less, still further more preferably 0.14 mg/u or less, particularly preferably 0.13 mg/u or less. A specific range of the magnesium chloride content is, not limitatively, from 0.01 to 1.0 mg/u, from 0.01 to 0.50 mg/u, from 0.01 to 0.20 mg/u, from 0.01 to 0.18 mg/u, from 0.01 to 0.14 mg/u, from 0.01 to 0.13 mg/u, from 0.02 to 2.0 mg/u, from 0.02 to 1.0 mg/u, from 0.02 to 0.50 mg/u, from 0.02 to 0.20 mg/u, from 0.02 to 0.18 mg/u, from 0.02 to 0.14 mg/u, from 0.02 to 0.13 mg/u, from 0.03 to 2.0 mg/u, from 0.03 to 1.0 mg/u, from 0.03 to 0.50 mg/u, from 0.03 to 0.20 mg/u, from 0.03 to 0.18 mg/u, from 0.03 to 0.14 mg/u, from 0.03 to 0.13 mg/u, from 0.04 to 2.0 mg/u, from 0.04 to 1.0 mg/u, from 0.04 to 0.50 mg/u, from 0.04 to 0.20 mg/u, from 0.04 to 0.18 mg/u, from 0.04 to 0.14 mg/u, from 0.04 to 0.13 mg/u, from 0.05 to 2.0 mg/u, from 0.05 to 1.0 mg/u, from 0.05 to 0.50 mg/u, from 0.05 to 0.20 mg/u, from 0.05 to 0.18 mg/u, from 0.05 to 0.14 mg/u, from 0.05 to 0.13 mg/u, from 0.06 to 2.0 mg/u, from 0.06 to 1.0 mg/u, from 0.06 to 0.50 mg/u, from 0.06 to 0.20 mg/u, from 0.06 to 0.18 mg/u, from 0.06 to 0.14 mg/u, from 0.06 to 0.13 mg/u, from 0.07 to 2.0 mg/u, from 0.07 to 0.20 mg/u, from 0.07 to 1.0 mg/u, from 0.07 to 0.50 mg/u, from 0.07 to 0.18 mg/u, from 0.07 to 0.14 mg/u, from 0.07 to 0.13 mg/u, from 0.08 to 2.0 mg/u, from 0.08 to 1.0 mg/u, from 0.08 to 0.50 mg/u, from 0.08 to 0.20 mg/u, from 0.08 to 0.18 mg/u, from 0.08 to 0.14 mg/u, or from 0.08 to 0.13 mg/u.

Further, from the standpoint of preferably obtaining powder characteristics (e.g., inhibitory properties of caking and/or deliquescence) of the dry protein deamidase composition in addition to the stability-improving effect, the amount per unit activity of the protein deamidase is, for example, from 0.02 to 0.12 mg/u. From the standpoint of more preferably obtaining powder characteristics (e.g., inhibitory properties of caking and/or deliquescence) of the dry protein deamidase composition, the more preferable upper limit of a range of the above amount per unit activity of the protein deamidase is, not limitatively, 0.12 mg/u or less, preferably 0.11 mg/u or less, more preferably 0.10 mg/u or less, further more preferably 0.09 mg/u or less, still further more preferably 0.08 mg/u or less. A specific range of the magnesium chloride content, when taking into consideration the powder characteristics of the dry protein deamidase composition in addition to the stability-improving effect, is, not limitatively, from 0.02 to 0.11 mg/u, 0.02 to 0.10 mg/u, 0.02 to 0.09 mg/u, or 0.02 to 0.08 mg/u.

[1-3. Calcium Chloride]

The dry protein deamidase composition of the present invention may further include calcium chloride. Calcium chloride can be used as a powder characteristic-improving agent and/or a stabilizing aid. The dry protein deamidase composition of the present invention can obtain the more excellent powder characteristics (e.g., inhibitory properties of caking and/or deliquescence) by using both calcium chloride and magnesium chloride.

The content of calcium chloride is not particularly limited. However, from the standpoint of preferably improving the powder characteristics of the dry protein deamidase composition, a ratio of calcium chloride with respect to the total weight of the dry protein deamidase composition is, for example, 1.0% by weight or more, preferably 2.0% by weight or more, more preferably 2.5% by weight or more, and, for example, 10.0% by weight or less, preferably 8.0% by weight or less, more preferably 6.5% by weight or less, further more preferably 6.0% by weight or less, still further more preferably 5.5% by weight or less. A specific range of the calcium chloride content is, not limitatively, from 1.0 to 10.0% by weight, from 1.0 to 8.0% by weight, from 1.0 to 6.5% by weight, from 1.0 to 6.0% by weight, from 1.0 to 5.5% by weight, from 2.0 to 10.0% by weight, from 2.0 to 8.0% by weight, from 2.0 to 6.5% by weight, from 2.0 to 6.0% by weight, from 2.0 to 5.5% by weight, from 2.5 to 10.0% by weight, from 2.5 to 8.0% by weight, from 2.5 to 6.5% by weight, from 2.5 to 6.0% by weight, or from 2.5 to 5.5% by weight.

Further, from the standpoint of preferably improving the powder characteristics of the dry protein deamidase composition, the amount with respect to 100 parts by weight of the total amount of magnesium chloride and calcium chloride is, for example, 15 parts by weight or more, preferably 30 parts by weight or more, more preferably 35 parts by weight or more, and, for example, 95 parts by weight or less, preferably 90 parts by weight or less, more preferably 85 parts by weight or less, further more preferably 70 parts by weight or less, still more preferably 65 parts by weight or less. A specific range of the amount with respect to 100 parts by weight of the total amount of magnesium chloride and calcium chloride is, not limitatively, from 15 to 95 parts by weight, from 15 to 90 parts by weight, from 15 to 85 parts by weight, from 15 to 70 parts by weight, from 15 to 65 parts by weight, from 30 to 95 parts by weight, from 30 to 90 parts by weight, from 30 to 85 parts by weight, from 30 to 70 parts by weight, from 30 to 65 parts by weight, from 35 to 95 parts by weight, from 35 to 90 parts by weight, from 35 to 85 parts by weight, from 35 to 70 parts by weight, or from 35 to 65 parts by weight.

[1-4. Other Components]

The dry protein deamidase composition of the present invention may include other components other than the above components. Examples of the other components include a saccharide excipient such as dextrin, indigestible dextrin, starch, potato starch, corn starch, sucrose, mannitol, sorbitol, lactose, or trehalose; a salt such as sodium chloride or calcium chloride; an antiseptic such as a para-hydroxybenzoic acid ester, chlorobutanol, or benzyl alcohol; an antioxidant; various proteins (excluding the protein deamidase) such as a milk protein, a soybean protein, and a wheat protein; a peptide, an amino acid; a lactic acid bacterium; a vitamin; a mineral (excluding the above salts); oil and fat; various kinds of extract (meat extract, yeast extract, etc.); and a nucleic acid.

[1-5. pH upon Dissolution in Water]

In a case where the dry protein deamidase composition of the present invention is the stabilized dry protein deamidase composition including the protein deamidase and magnesium chloride, the pH (the pH at 25° C., hereinafter the same) of the dry protein deamidase composition upon dissolution in water at a concentration of 1 w/v % is not particularly limited. The pH is, for example, 2 or higher, and 8 or lower, and a specific range of the pH is, not limitatively, from 2 to 8. Further, from the standpoint of more effectively obtaining the stability-improving effect by magnesium chloride as compared with the case of not including magnesium chloride, the pF1 upon dissolution in water is preferably 4 or higher, and preferably 8 or lower, and a specific range of the PH is, not limitatively, from 4 to 8.

In a case where the dry protein deamidase composition of the present invention is the stabilized dry protein deamidase composition having a pH of 2 or higher and lower than 5 upon dissolution in water at a predetermined concentration, the pH (the pH at 25° C., hereinafter the same) of the dry protein deamidase composition upon dissolution in water at a concentration of 1 w/v % is 2 or higher and lower than 5 from the standpoint of obtaining the stability-improving effect of the dry protein deamidase composition. From the standpoint of more preferably obtaining the stability-improving effect, the upper limit of a range of the pH is preferably 4 or lower, more preferably 3 or lower. A specific range of the pH is, not limitatively, from 2 to 4 (2 or higher and 4 or lower) or from 2 to 3. The protein deamidase composition in a liquid state is stable at pH 5 to 9. On the other hand, in the protein deamidase composition of the present invention prepared in a dry state, the stability of the protein deamidase can be improved by having a pH of 2 or higher and lower than 5 upon dissolution in water as compared with the case of having a pH of from 5 to 9 upon dissolution in water. The dry protein deamidase composition of the present invention having a p1-I of 2 or higher and lower than 5 upon dissolution in water can obtain the stability-improving effect of the protein deamidase without including magnesium chloride described above.

[1-6. Form]

The form of the dry protein deamidase composition of the present invention is not particularly limited as long as it is in a dry state. Examples thereof include a powdery form and a granular form, with a powdery form being preferable. Further, the dry protein deamidase composition of the present invention is formed, for example, as a spray-dried product, a freeze-dried product, and a vacuum-dried product, with a spray-dried product and a freeze-dried product being preferable.

[1-7. Production Method]

The dry protein deamidase composition includes a step of preparing the protein deamidase, a step of preparing an enzyme liquid containing the protein deamidase, and a step of drying the enzyme liquid.

[1-7-1. Step of Preparing Protein Deamidase]

In the step of preparing the protein deamidase, the protein deamidase can be appropriately produced by the person skilled in the art from the source organism described in the above "1-1. Protein deamidase" using a known culture method. Examples of the culture method include a solid culture method and a liquid culture method, and a liquid culture method is preferably used.

A medium is not particularly limited as long as a medium can grow a microorganism in use. Any medium can be used as long as a microorganism producing the protein deamidase can grow and produce the protein deamidase. For example, a medium o which the following substance is added can be used: a carbon source such as glucose, sucrose, glycerol, dextrin, molasses, or an organic acid; further, a nitrogen source such as ammonium sulfate, ammonium carbonate, ammonium phosphate, ammonium acetate, or peptone, yeast extract, corn steep liquor, a casein hydrolysate, or meat extract; further, an inorganic salt such as a potassium salt, a magnesium salt, a sodium salt, a phosphate salt, a manganese salt, a ferric salt, or a zinc salt.

The pH of the medium is adjusted to, for example, approximately from 3 to 9, preferably approximately from 5.0 to 8.0, the culture temperature is normally approximately from 10 to 50° C., preferably approximately from 20 to 37° C., and the culture is performed under an aerobic condition for from 12 hours to 20 days, preferably approximately from 1 to 7 days. Examples of the culture method that can be used include a shake culture method and an aerobic submerged culture method using a jar fermenter.

The protein deamidase of the present invention can be obtained by isolating the protein deamidase from the obtained culture liquid using an ordinary means. For example, for isolating and purifying the protein deamidase from the culture liquid, the culture liquid is processed by a routine procedure in combination of centrifugal separation, UF concentration, salting out, and various types of chromatography using, for example, an ion-exchanging resin. As a result, the purified protein deamidase can be obtained.

Further, a commercially available protein deamidase (e.g., Protein-glutaminase "Amano" 500 available from Amano Enzyme Inc., etc.) may be used as a starting material.

[1-7-2. Step of Preparing Enzyme Liquid]

In a case where the stabilized dry protein deamidase composition including the protein deamidase and magnesium chloride is produced, in the step of preparing the enzyme liquid, the protein deamidase is prepared as an enzyme liquid including magnesium chloride and, if necessary, a component selected from the group consisting of calcium chloride and other components described above. For preparing the enzyme liquid, for example, magnesium chloride can be included in an amount of, for example, from 1.0 to 10.0% by weight with respect to the total weight (expressed in terms of dry weight) of the materials or in an amount of, for example, from 0.01 to 2.0 mg/u as an amount per unit activity of the protein deamidase. More specifically, magnesium chloride can be included in the amount described in the above "1-2. Magnesium chloride". Further, in such a case, the pH of the enzyme liquid is not particularly limited, and the pH is, for example, 2 or higher, and 8 or lower. Further, from the standpoint of more effectively obtaining the stability-improving effect by magnesium chloride as compared with the case of not including magnesium chloride, the pH of the enzyme liquid is adjusted to preferably 4 or higher, and preferably 8 or lower. More specifically, the pH described in the above "1-5. pH upon dissolution in water" can be mentioned. Further, in a case where calcium chloride is included, calcium chloride can be included in an amount of, for example, 1.0% by weight or more, and 10.0% by weight or less, as a ratio of calcium chloride with respect to the total dry weight of the materials, or in an amount of 15 parts by weight or more, and 85 parts by weight or less, with respect to 100 parts by weight of the total amount of magnesium chloride and calcium chloride. More specifically, calcium chloride can be included in the amount described in the above "1-2. Calcium chloride".

In a case where the stabilized dry protein deamidase composition having a pH of 2 or higher and lower than 5 upon dissolution in water in a predetermined concentration is produced, in the step of preparing the enzyme liquid, the pH of the enzyme liquid can be adjusted to 2 or higher and lower than 5, and, from the standpoint of preferably obtaining the stability-improving effect of the dry protein deamidase composition, the pH can be adjusted to preferably from 2 to 4, more preferably from 2 to 3.

[1-7-3. Step of Drying Enzyme Liquid]

In the step of drying the enzyme liquid, the enzyme liquid obtained in the above step is dried. Examples of a drying method include a freeze-drying method, a vacuum-drying method, and a spray-drying method. By this step, the dry protein deamidase composition is obtained.

[1-8. Application]

The dry protein deamidase composition of the present invention can directly deamidate an amide group in a protein upon acting on various proteins. The resulting deamidated protein shows a reduction in pI and an increase in hydration force and electrostatic repulsion with an increase in negative charges. Further, a change in the higher-order structure of the protein causes an increase in surface hydrophobicity. These effects can improve protein functionalities such as improvement in solubility and dispersibility, improvement in foamability and foam stability, and improvement in emulsifiability and emulsion stability.

Thus, the dry protein deamidase composition of the present invention can be widely used in a food field. Specifically, the following applications can be exemplified: an application for improving solubility, dispersibility, emulsifiability, or the like of a vegetable protein in a weakly acidic condition environment corresponding to a pH range of ordinary foods (e.g., an application for producing an acidic beverage such as coffee whitener or juice, dressing, mayonnaise, and cream); an enhancement in solubility and dispersibility of a hardly soluble vegetable protein (e.g., an application for producing tempura flour using wheat gluten and the like); an application for modifying dough in making bread and confectionery (e.g., an application for producing a cracker, a biscuit, a cookie, and crust of a pizza or a pie); an application for removing or reducing an allergen of an allergenic protein in a food (e.g., an application for producing a food for a patient with wheat allergy); an application for reducing mineral sensitivity of a protein and increasing the soluble mineral content in a liquid containing the protein and a mineral, thereby improving the absorption of the mineral into a human body (e.g., an application for producing a high-mineral (e.g., calcium)-content beverage and a mineral (e.g., calcium) absorption promoter); an application for reducing a bitter taste, an application for increasing a rate of proteolysis by a protease, and/or an application for increasing the glutamic acid content (e.g., an application for producing an amino acid-based seasoning (hydrolyzed animal protein (HAP), hydrolyzed vegetable protein (HVP)), and miso and soy sauce).

[2. Method for Improving Stability]

The present invention also provides a method for improving stability of the protein deamidase in the dry enzyme composition including the protein deamidase. Specifically, the stability-improving method of the present invention is characterized in that the protein deamidase coexists with magnesium chloride in the dry enzyme composition. Alternatively, the stability-improving method of the present invention is characterized by adjusting the pH of the dry enzyme composition including the protein deamidase to 2 or higher and lower than 5 upon dissolution in water at 1 w/v % (specifically, as described in the step of preparing the enzyme liquid in the above production method of the dry protein deamidase composition, this can be performed by adjusting the pH of the enzyme liquid to 2 or higher and lower than 5).

Note that, as described in Examples below, the stability can be measured, for example, from the remaining activity or the like after storage under a predetermined condition. The stability of the stabilized dry protein deamidase composition is not particularly limited as long as the stability is improved as compared with a case of not performing the stability-improving method. The remaining activity after storage for 1 month at 40° C. is, for example, 60% or more, preferably 65% or more, more preferably 70% or more, further more preferably 75% or more, still further more preferably 80% or more. Note that, in the above description, the case of not performing the stability-improving method corresponds, in the form characterized in that the protein deamidase coexists with magnesium chloride, to a case of not including magnesium chloride in the dry protein deamidase composition, while it corresponds, in the form characterized in that the pH of the dry enzyme composition upon dissolution in water at 1 w/v % is adjusted to 2 or higher and lower than 5, to a case of adjusting the pH to 5 or higher in the dry protein deamidase composition.

In the stability-improving method of the present invention, the kind and content of component in use, the pH upon dissolution in water, the production method and form of the dry enzyme composition, and the like are as described in the above section "1. Dry protein deamidase composition".

EXAMPLES

Hereinafter, the present invention will be described further in detail by way of Examples. However, the present invention is not limited to the following Examples.

[Preparation of Protein Deamidase]

In the following Test examples, as the protein deamidase, a protein deamidase preparation "Protein-glutaminase "Amano" 500" (derived from *Chryseobacterium* genus) 500 u/g manufactured by Amano Enzyme Inc. was used. The "Protein-glutaminase "Amano" 500" is an enzyme preparation of which activity is adjusted to 500 u/g by including dextrin in addition to the protein deamidase. Note that the protein deamidase may also be acquired by the following method. *Chryseobacterium* sp. No. 9670 is cultured with shaking in an LB base medium (manufactured by Gibco) at 25° C. for 2 to 7 days in accordance with the method described in Patent document 2, and then a supernatant was obtained by centrifugation. After completing the culture, the culture liquid was subjected to centrifugal separation (12000 rpm, 4° C., 20 min.) to obtain a supernatant as a crude enzyme liquid. The supernatant was processed through ultra-filtration (UF) concentration (SEP-0013), salting out, Phenyl Sepharose, and Sephacryl S-100 to purify the enzyme.

[Measuring Method of Protein Deamidase Activity in Composition Containing Protein Deamidase]

In the following Test examples, the protein deamidase activity in the composition containing the protein deamidase was measured as follows. Note that, in the following description, a substrate Z-Gln-Gly represents N-benzyloxy-carbonyl-L-glutaminylglycine.

1. To 1.0 ml of 0.2M phosphate buffer solution (pH 6.5) containing 34 mM Z-Gln-Gly, 0.1 ml of a sample solution appropriately diluted with 0.2M phosphate buffer solution (pH 6.5) containing 0.002% Triton-X was added, followed by incubation at 37° C. for 10 min. Then, the reaction was terminated by adding 1.0 ml of 0.4 M trichloroacetic acid.

2. The amount of free ammonia was quantified using an ammonia test kit (manufactured by Wako Pure Chemical Industries, Ltd.).

Specifically, after mixing 0.2 ml of the reaction liquid with 0.8 ml of purified water, 1.0 ml of a chromogen reagent A (a solution containing 0.43 M phenol and 0.5 M sodium pentacyanonitrileferrate (III) dihydrate) was added to the mixture and mixed. Further, 0.5 ml of a chromogen reagent B (0.89 M potassium hydroxide aqueous solution) was added to the mixture and mixed. After 1.0 ml of a chromogen reagent C (an aqueous solution containing potassium carbonate and sodium hypochlorite) was added to the mixture and mixed, the mixture was incubated at 37° C. for 20 min. Subsequently, absorbance (A1) at a wavelength of 630 nm was measured.

3. As a blank. 1.0 ml of 0.4 M trichloroacetic acid was added to 0.1 ml of the sample solution and then 1.0 ml of 0.2 M phosphate buffer solution (pH 6.5) containing 30 mM Z-Gln-Gly was added to the mixture and mixed. The resulting mixture solution was also subjected to the color developing operation in the same manner and absorbance (A2) was measured.

4. The amount of enzyme required to produce 1 μmol ammonia per minute was defined as 1 u, and the protein deamidase activity (PG activity) was calculated by the following formula.

$$\text{PG activity (u/g)} = F = (A1 - A2) \times (1/17.03) \times (2.1/0.1) \times (1/10) \times N$$

F: constant calculated by creating calibration curve of ammonia
17.03: molecular weight of ammonia
2.1: total amount of reaction liquid
0.1: adding amount of sample
10: reaction time (min.)
N: dilution factor

[Test Example 1: Verification of Stability-Improving Effect by Magnesium Chloride-1]

(1) Preparation of Dry Protein Deamidase Composition

The enzyme liquid was obtained by dissolving "Protein-glutaminase "Ammo" 500" (manufactured by Amano Enzyme Inc.) (500 u/g) in water and also dissolving therein magnesium chloride in accordance with formulation described in Table 1 (a weight ratio with respect to the total weight (expressed in terms of dry weight) of the protein deamidase preparation including the protein deamidase, dextrin, and magnesium chloride and a weight of the protein deamidase preparation per unit activity of the protein deamidase). Further, as Comparative example, the enzyme liquid without magnesium chloride (no addition) and the enzyme liquid in which magnesium chloride was replaced with cysteine or calcium chloride were prepared in the same manner in accordance with formulation described in Table 1 (the weight ratio with respect to the total weight (expressed in terms of dry weight) of the protein deamidase preparation including the protein deamidase and dextrin or the protein deamidase preparation including the protein deamidase, dextrin, and cysteine or calcium chloride, and the weight per unit activity of the protein deamidase). These enzyme liquids were adjusted to pH 6.0 (25° C.) using 1M hydrochloric acid and 1M sodium hydroxide.

The enzyme liquid (after pH adjustment) was powdered using a spray dryer (EYELA SPRAY DRYER SD-1000) to obtain the dry pr in deamidase composition as a spray-dried product.

(2) Evaluation of Stability

The spray-dried products thus obtained were each put into a GX film bag (manufactured by TOPPAN PRINTING CO., LTD.), and the bags were sealed by heat sealing and then stored for 2 days at temperature conditions of −20° C. and 60° C. The protein deamidase activity after storage was measured and the remaining activity (%) was derived as a percentage of the protein deamidase activity at 60° C. with respect to the protein deamidase activity at −20° C.

The result is shown in Table 1. The stability was improved in the case of including magnesium chloride (Example 1) as compared with the case of not including magnesium chloride (Comparative example 1), the case of including cysteine instead of magnesium chloride (Comparative example 2), and the case of including calcium chloride instead of magnesium chloride (Comparative example 3). This confirmed that magnesium chloride exhibited an excellent stabilizing effect on the dry protein deamidase composition.

TABLE 1

| | Stabilizing agent | Weight ratio with respect to total weight (in terms of dry weight) | Weight per unit activity | Remaining activity |
|---|---|---|---|---|
| Comparative example 1 | No addition | — | — | 40% |
| Comparative example 2 | Cysteine | 6.5% | 0.13 mg/u | 38% |
| Comparative example 3 | Calcium chloride | 6.5% | 0.13 mg/u | 62% |
| Example 1 | Magnesium chloride | 6.5% | 0.13 mg/u | 72% |

[Test Example 2: Verification of Stability-Improving Effect by Magnesium Chloride 2]

(1) Preparation of Dry Protein Deamidise Composition

The dry protein deamidase composition (Example 2) was prepared as a spray-dried product in the same a as in Test example 1 except that the weight ratio of magnesium chloride was changed to 2.5% by weight, and the composition was subjected to the following stability evaluation test. Further, the dry protein deamidase composition with no addition (Comparative example 1) and the dry protein deamidase composition having the weight ratio of 6.5% by weight (Example 1), obtained in Test example 1, were also subjected to the following stability evaluation test.

(2) Evaluation of Stability

The spray-dried products thus obtained were each put into a GX film bag (manufactured by TOPPAN PRINTING CO., LTD.), and the bags were sealed by heat sealing and then stored for 1 month at temperature conditions of −20° C. and 40° C. The protein deamidase activity after storage was measured and the remaining activity (%) was derived as a percentage of the protein deamidise activity at 40° C. with respect to the protein deamidase activity at −20° C.

Table 2 shows the results of the stability evaluation of the dry protein deamidase composition with no addition (Comparative example 1) and the dry protein deamidase composition having the weight ratio of 2.5% by weight (Example 2) or 6.5% by weight (Example 1). As shown in Table 2, the stabilizing effect of the dry protein deamidase composition was confirmed in both Examples. This confirmed that magnesium chloride exhibited an excellent stabilizing effect on the dry protein deamidase composition

TABLE 2

| | Stabilizing agent | Weight ratio with respect to total weight (in terms of dry weight) | Weight per unit activity | Remaining activity |
|---|---|---|---|---|
| Comparative example 1 | No addition | — | — | 50% |
| Example 2 | Magnesium chloride | 2.5% | 0.05 mg/u | 66% |
| Example 1 | Magnesium chloride | 6.5% | 0.13 mg/u | 92% |

[Test Example 3: Verification of Powder Characteristics-Improving Effect by Using Both Magnesium Chloride and Calcium Chloride]ps (1) Preparation of Dry Protein Deamidase Composition The enzyme liquid was obtained by dissolving "Protein-glutaminase "Ammo" 500" (manufactured by Amano Enzyme Inc.) (500 u/g) in water and also dissolving therein magnesium chloride, or magnesium chloride and calcium chloride in accordance with formulation described in Table 3 (the weight ratio with respect to the total weight (expressed in terms of dry weight) of the protein deamidase preparation including the protein deamidase, dextrin, magnesium chloride, and with or without calcium chloride, and the weight of the protein deamidase preparation per unit activity of the protein deamidase). The enzyme liquids were adjusted to pH 6 (25° C.) using 1M hydrochloric acid and 1M sodium hydroxide.

The enzyme liquid (after pH adjustment) was powdered using a spray dryer (EYELA SPRAY DRYER SD-1000) to obtain the dry protein deamidase composition as a spray-dried product.

(2) Evaluation of Stability

The spray-dried products thus obtained were each put into a GX film bag (manufactured by TOPPAN PRINTING CO., LTD.), and the bags were sealed by heat sealing and then stored for 1 month at temperature conditions of −20° C. and 40° C. The protein deamidase activity after storage was measured and the remaining activity (%) was derived as a percentage of the protein deamidase activity at 40° C. with respect to the protein deamidase activity at −20° C.

(3) Evaluation of Powder Characteristics

The spray-dried products thus obtained were each put into a GX film bag (manufactured by TOPPAN PRINTING CO., LTD.), and the bags were sealed by heat sealing and then stored for 1 month at a temperature condition of 40° C. After that, the appearance of the powders was visually observed to evaluate powder characteristics on the basis of the following criteria.

○: neither caking nor deliquescence was observed

Δ: mild caking or deliquescence was observed x: severe caking or deliquescence was observed The result is shown in Table 3. In the case of magnesium chloride alone (Example 1), the mild caking that was not observed in the case of no addition (Comparative example 1) was observed. However, the level of the caking was acceptable as the dry enzyme composition. In the case of using both magnesium chloride and calcium chloride (Examples 3 to 5), the stability was on a declining trend as compared with the case of magnesium chloride alone (Example 1). However, the stability was still maintained at an excellent level, and, furthermore, it was confirmed that the caking of the dry protein deamidase composition was reduced and the powder characteristics were improved.

TABLE 3

| | Stabilizing agent | Weight ratio with respect to total weight (in terms of dry weight) | Weight per unit activity | Remaining activity | Powder characteristics |
|---|---|---|---|---|---|
| Comparative example 1 | No addition | — | — | 50% | ○ |
| Example 1 | Magnesium chloride | 6.5% | 0.13 mg/u | 92% | Δ |
| Example 3 | Magnesium chloride | 4.0% | 0.08 mg/u | 84% | ○ |
| | Calcium chloride | 2.5% | 0.05 mg/u | | |
| Example 4 | Magnesium chloride | 2.5% | 0.05 mg/u | 81% | ○ |
| | Calcium chloride | 4.0% | 0.08 mg/u | | |
| Example 5 | Magnesium chloride | 1.0% | 0.02 mg/u | 82% | ○ |
| | Calcium chloride | 5.5% | 0.11 mg/u | | |

[Test Example 4: Verification of Effect of pH Upon Dissolution on Stability of Dry Composition]

(1) Preparation of Dry Protein Deamidase Composition

The enzyme liquid was obtained by dissolving "Protein-glutaminase "Amano" 500" (manufactured by Amano Enzyme Inc.) (500 u/g) in water and also dissolving therein magnesium chloride and calcium chloride in accordance with formulation described in Table 4 (the weight ratio with respect to the total weight (expressed in terms of dry weight) of the protein deamidase preparation including the protein deamidase, dextrin, magnesium chloride, and calcium chloride and the weight of the protein deamidase preparation per unit activity of the protein deamidase). Note that, in an example described as "No addition" in Table 4, the enzyme liquid containing neither magnesium chloride nor calcium chloride was obtained. The pH (25° C.) of these enzyme liquids were adjusted to 2, 3, 4, 5, 6, 7, or 8 using 1M hydrochloric acid and/or 1M sodium hydroxide.

The enzyme liquid (after pH adjustment) was powdered using a spray dryer (EYELA SPRAY DRYER SD-1000) to obtain the dry protein deamidase composition as a spray-dried product.

Note that, when the obtained dry protein deamidase compositions (each obtained from the enzyme liquids at pH 2, 3, 4, 5, 6, 7, and 8) were redissolved in water at 1 w/v % again, the pH (25° C.) of the compositions after redissolution remained the same at 2, 3, 4, 5, 6, 7, and 8.

(2) Evaluation of Stability

The spray-dried products thus obtained were each put into a GX film bag (manufactured by TOPPAN PRINTING CO., LTD.), and the bags were sealed by heat sealing and then stored for 1 month at temperature conditions of −20° C. and 40° C. The protein deamidase activity after storage was measured and the remaining activity (%) was derived as a percentage of the protein deamidase activity at 40° C. with respect to the protein deamidase activity at −20° C.

The result is shown in Table 4. As for the dry protein deamidase compositions containing neither magnesium chloride nor calcium chloride, it was confirmed that the dry protein deamidase compositions having a pH of from 2 to 4 at the time of the enzyme liquid (Examples 6 to 8) had the higher stability than the dry protein deamidase compositions having a pH of from 5 to 8 at the time of the enzyme liquid (Comparative examples 4 to 7). In particular, it was confirmed that the dry protein deamidase compositions having a pH of from 2 to 3 at the time of the enzyme liquid (Examples 6 and 7) had the significantly high stability. On the other hand, when the dry protein deamidase compositions containing magnesium chloride and calcium chloride (Examples 9 to 15) were compared with the dry protein deamidase compositions with no addition (Examples 6 to 8 and Comparative examples 4 to 7) at the same pH levels at the time of the enzyme liquid, the former stability was improved in all cases. The degree of improvement in the former stability in the comparison with the dry protein deamidase compositions with no addition was particularly significant at pH 4 to 8.

TABLE 4

| | Stabilizing agent | Weight ratio with respect to total weight (in terms of dry weight) | Weight per unit activity | pH at the time of enzyme liquid | Remaining activity |
|---|---|---|---|---|---|
| Example 6 | No addition | — | — | 2 | 99% |
| Example 7 | | | | 3 | 93% |
| Example 8 | | | | 4 | 72% |
| Comparative example 4 | | | | 5 | 57% |
| Comparative example 5 | | | | 6 | 50% |
| Comparative example 6 | | | | 7 | 42% |
| Comparative example 7 | | | | 8 | 38% |
| Example 9 | Magnesium chloride + Calcium chloride | 2.5% (Magnesium chloride) 4.0% (calcium chloride) | 0.05 mg/u (Magnesium chloride) 0.08 mg/u (Calcium chloride) | 2 | 102% |
| Example 10 | | | | 3 | 94% |
| Example 11 | | | | 4 | 95% |
| Example 12 | | | | 5 | 84% |
| Example 13 | | | | 6 | 73% |
| Example 14 | | | | 7 | 73% |
| Example 15 | | | | 8 | 70% |

[Test Example 5: Liquid Product]
(1) Preparation of Liquid Protein Deamidase Composition The enzyme liquid was obtained by dissolving "Protein-glutaminase "Amano" 500" (manufactured by Amano Enzyme Inc.) (500 u/g) in water at a Brix value of 25% and also dissolving therein magnesium chloride and calcium chloride in the amounts described in Table 5 (the amount with respect to the total weight (expressed in terms of dry weight) of the protein deamidase, dextrin, magnesium chloride, and calcium chloride and the weight of the dry preparation per unit activity of the protein deamidase Note that, in an example described as "No addition" in Table 6, the enzyme liquid containing neither magnesium chloride nor calcium chloride was obtained. The pH (25° C.) of the enzyme liquids were adjusted to 6 or 7 using 1M hydrochloric acid and/or 1M sodium hydroxide to obtain liquid protein deamidase compositions.

(2) Evaluation of Stability

The obtained liquid products were put into polypropylene tubes, covered with lids, and then stored for 1 month at 40° C. The protein deamidase activity after storage was measured and the remaining activity (%) was derived as a percentage of the protein deamidase activity after storage with respect to the protein deamidase activity before storage.

The result is shown in Table 5. As for the liquid compositions, the stability of both the liquid compositions with no addition (Comparative examples 8 and 9) and the liquid compositions containing magnesium chloride and calcium carbonate (Comparative examples 10 and 11.) was reduced at low pH. On the other hand, as shown in the above Table 4, the stability of the powder compositions was, conversely, increased with a lower pH at the time of the enzyme liquid. That is, it was confirmed that the effect of the pH on the stability was completely different between the liquid compositions and the powder compositions.

Further, when the liquid compositions containing magnesium chloride and calcium chloride (Comparative examples 10 and 11) were compared with the liquid compositions with no addition (Comparative examples 8 and 9) at the same pH levels, the former stability was reduced in both cases. On the other hand, as shown in the above Table 1 to Table 4, the stability of the powder composition containing magnesium chloride, or magnesium chloride and calcium chloride was, conversely, higher than that of the powder composition with no addition. That is, it was confirmed that the effect of magnesium chloride and calcium chloride on the stability was completely different between the liquid compositions and the dry compositions.

TABLE 5

| | Stabilizing agent | Weight ratio with respect to total weight (in terms of dry weight) | Weight per unit activity (in terms of dry weight) | pH at the time of enzyme liquid | Remaining activity |
| --- | --- | --- | --- | --- | --- |
| Comparative example 8 | No addition | — | — | 6 | 54% |
| Comparative example 9 | | | | 7 | 99% |
| Comparative example 10 | Magnesium chloride + | 2.5% (Magnesium chloride) | 0.05 mg/u (Magnesium chloride) | 6 | 48% |
| Comparative example 11 | Calcium chloride | 4.0% (Calcium chloride) | 0.08 mg/u (Calcium chloride) | 7 | 61% |

The preferable embodiments of the present invention have been described above. The present invention is not limited to these embodiments and the embodiments may be modified in various ways without departing from the gist of the present invention.

What is claimed is:

1. A dry stabilized composition comprising a dry protein deamidase and magnesium chloride,
   wherein the dry stabilized composition has a deamidation activity after storage for one month at 40° C. of at least 60% as compared to a deamidation activity of the dry stabilized composition stored for one month at −20° C.,
   wherein an amino acid sequence of the protein deamidase has identity of 80% or more with the amino acid sequence represented by SEQ ID NO: 1 or 2, and
   wherein a content of the magnesium chloride in the dry stabilized composition is from 2.5% to 6.5% by weight.

2. The dry stabilized composition according to claim 1, wherein a content of the magnesium chloride is from 0.05 to 0.13 mg/u.

3. A stability-improving method for improving stability of a protein deamidase in a dry enzyme composition including the protein deamidase, wherein the protein deamidase coexists with the magnesium chloride in the dry enzyme composition, or
   a pH of the dry enzyme composition upon dissolution in water at 1 w/v % is adjusted to 2 or higher and lower than 5.

4. A dry stabilized composition comprising a dry protein deamidase having a pH of 2 or higher and 4 or lower upon dissolution in water at 1 w/v %,
   wherein the dry stabilized composition has a deamidation activity after storage for one month at 40° C. of at least 60% as compared to a deamidation activity of the dry stabilized composition stored for one month at −20° C.,
   wherein an amino acid sequence of the protein deamidase has an identity of 80% or more with an amino acid sequence represented by SEQ ID NO: 1 or 2, and
   wherein a stabilizing agent other than an agent for adjusting the pH is not added.

* * * * *